US011813430B2

(12) United States Patent
Tu

(10) Patent No.: US 11,813,430 B2
(45) Date of Patent: Nov. 14, 2023

(54) MULTI-CHANNEL AUTOMATIC PUMP

(71) Applicant: ZHEJIANG MDKINGDOM TECHNOLOGY CO., LTD., Lishui (CN)

(72) Inventor: Jianguang Tu, Lishui (CN)

(73) Assignee: ZHEJIANG MDKINGDOM TECHNOLOGY CO., LTD., Lishui (CN)

( * ) Notice: Subject to any disclaimer, the term of this patent is extended or adjusted under 35 U.S.C. 154(b) by 212 days.

(21) Appl. No.: 17/479,305

(22) Filed: Sep. 20, 2021

(65) Prior Publication Data

US 2022/0088299 A1    Mar. 24, 2022

(30) Foreign Application Priority Data

Sep. 22, 2020   (CN) .......................... 202010999409.4

(51) Int. Cl.
*A61M 5/168*    (2006.01)
*A61M 5/142*    (2006.01)

(52) U.S. Cl.
CPC ........ *A61M 5/16827* (2013.01); *A61M 5/142* (2013.01); *A61M 5/16813* (2013.01); *A61M 5/16822* (2013.01)

(58) Field of Classification Search
CPC .............. A61M 5/16827; A61M 5/142; A61M 5/16813; A61M 5/16822; A61M 5/365; A61M 5/14; A61M 5/168; A61M 5/16804; A61M 5/36
See application file for complete search history.

(56) References Cited

U.S. PATENT DOCUMENTS

2018/0036480 A1* 2/2018 Riphagen .............. A61M 5/385
2019/0175828 A1* 6/2019 List ................... A61M 5/16831
2021/0346610 A1* 11/2021 Sekiguchi ......... A61M 5/16854

* cited by examiner

*Primary Examiner* — Jason E Flick
(74) *Attorney, Agent, or Firm* — WOMBLE BOND DICKINSON (US) LLP

(57) ABSTRACT

The invention provides a multi-channel automatic infusion pump, comprising: a pump body; a pump door; an infusion switching mechanism, an exhaust device and a bubble detection device arranged on the pump body; wherein the infusion switching mechanism includes a multi-channel liquid-stopping clamp, a liquid-stopping clamp fixing base and a driving structure; the multi-channel liquid-stopping clamp includes a body and N channels formed on the body, each channel includes a liquid-passing section and a liquid-stopping section, the liquid-passing section and the liquid-stopping section on each channel are arranged in a manner that any one of a plurality of upper branch tubes is located on the liquid-passing section of the corresponding channel while other upper branch tubes are located on the liquid-stopping section of the corresponding channel. The invention can access at least two bags of liquid medicine at one time, and has the advantages of simple operation, time and labor saving.

10 Claims, 9 Drawing Sheets

MULTI-CHANNEL AUTOMATIC PUMP

FIELD

The invention relates to an infusion pump, in particular to a multi-channel automatic infusion pump.

BACKGROUND

In the process of implementing infusion therapy in hospitals, there is often not only one bag of liquid medicine, but two bags or even more bags of liquid medicine. However, the current infusion pump products on the market can only be connected with one bag of liquid medicine at a time. The conventional operation is as follows: after the first bag of liquid medicine is infused, it must be changed by the medical staff, and the parameters must be reset according to the new fluid medicine, which is time-consuming and laborious, and also adds additional operational risks.

Therefore, there is an urgent need to provide an infusion pump structure that can access a plurality of bags of liquid medicine at a time, saving time and effort

SUMMARY

In view of the above technical problems, the present invention aims to provide a multi-channel automatic infusion pump, the infusion pump can be connected with at least two bags of liquid medicine at a time, with simple operation as well as time and labor saving.

The technical solution adopted by the present invention is as follows:

An embodiment of the present invention provides a multi-channel automatic infusion pump comprising: a pump body; a pump door; and an infusion switching mechanism, an exhaust device and a bubble detection device which are arranged on the pump body; an installation panel is formed at the front end of the pump body, and the pump door is movably connected with the installation panel to open or close the installation panel; the installation panel is connected with an infusion consumable to form a placement slot for placing the infusion consumable, the infusion consumable includes a multi-way connection joint and a plurality of upper branch tubes and one main tube respectively connected to both ends of the multi-way connection joint, the multi-way connection joint includes N branch tube joints and 1 main tube joint, wherein N≥2; the infusion switching mechanism includes a multi-channel liquid-stopping clamp, a liquid-stopping clamp fixing base and a driving structure, wherein the liquid-stopping clamp fixing base is fixed on the installation panel, the front end of the liquid-stopping clamp fixing base is provided with an insertion slot into which the multi-channel liquid-stopping clamp is inserted, the pump door is provided with a sliding slot for the multi-channel liquid-stopping clamp to slide, and the insertion slot and the sliding slot cooperate to form a sliding channel; the multi-channel liquid-stopping clamp includes a body and N channels formed on the body, each channel includes a liquid-passing section and a liquid-stopping section, wherein the liquid-passing section and the liquid-stopping section on each channel are arranged in a manner that any one of the upper branch tubes is located on the liquid-passing section of the corresponding channel while other upper branch tubes are located on the liquid-stopping section of the corresponding channel during the infusion; the driving structure is arranged at the upper end of the pump body and movably connected with the multi-channel liquid-stopping clamp for driving the multi-channel liquid-stopping clamp to move back and forth along the sliding channel, so as to make the upper branch tubes selectively communicate with the main tube; the exhaust device is used for squeezing the main tube to exhaust air in the main tube; and the bubble detection device is arranged on the installation panel and includes N upper branch tube bubble detection devices and one main tube bubble detection device.

Optionally, the infusion switching mechanism further comprises a detection plate arranged above the driving structure, the detection plate is provided with a sliding rheostat, and the driving structure is provided with a position detection point, and a sliding contact of the sliding rheostat is ganged-linked with the position detection point.

Optionally, the driving structure comprises: a motor; a push rod, a push rod attachment arm and a spring arranged in the liquid-stopping clamp fixing base, wherein the motor is connected with the rear end of the liquid-stopping clamp fixing base, the push rod is connected with the motor, the push rod attachment arm is movably arranged on both sides of the push rod, the spring is arranged between the rear end of the push rod attachment arm and the push rod, and a bent part is formed at the front end of the push rod attachment arm; the multi-channel liquid-stopping clamp is formed with a recessed part that matches the bent part; the insertion slot is arranged such that under the drive of the motor, the push rod attachment arm can be selectively combined with and separated from the multi-channel liquid-stopping clamp; and the position detection point is arranged on the push rod.

Optionally, the main tube is provided with a two-way connection joint.

Optionally, the sliding slot is provided with an elastic support structure in contact with the multi-channel liquid-stopping clamp, the elastic support structure includes two connecting rods and a supporting plate movably connected with two connecting rods, and a spring is arranged between the supporting plate and the connecting rod.

Optionally, it further includes a mechanical liquid-stopping clamp, wherein the mechanical liquid-stopping clamp is arranged at the lower end of the pump body for cooperating with the pump door so that the main tube is in a liquid-passing state or liquid-stopping state.

Optionally, the mechanical liquid-stopping clamp comprises a mechanical liquid-stopping clamp fixing base; a liquid-stopping knife clamp, a knife clamp spring, a liquid-stopping push rod and a push rod spring arranged on the mechanical liquid-stopping clamp fixing base; the front end of the liquid-stopping push rod extends out of the installation panel through the front end of the mechanical liquid-stopping clamp fixing base, and the rear end is connected with that of the mechanical liquid-stopping clamp fixing base through the push rod spring; the liquid-stopping knife clamp includes a liquid-stopping portion and a connecting portion connected by a connecting shaft, wherein the connecting portion is movably connected with the rear end of the liquid-stopping push rod, and the front end of the liquid-stopping portion is formed with a bent part, the pump door is formed with a limiting slot adapted to the bent part; the knife clamp spring is arranged between the rear end of the liquid-stopping part and the mechanical stop clamp fixing base.

Optionally, the rear end of the liquid-stopping push rod is formed with a hook that hooks the connecting portion.

Optionally, it further includes a controller, which is respectively communicatively connected with the exhaust device, the bubble detection device and the driving structure;

for the two adjacent upper branch tubes A and B, when the infusion of the upper branch tube A is the basic drug and the infusion of the upper branch tube B is the added therapeutic drug, the controller executes a control instruction to achieve the following steps:

S100: sending a first infusion instruction to the driving structure to drive the upper branch tube A to start the infusion while prohibiting infusion in the upper branch tube B;

S200: acquiring the infusion mass M of the upper branch tube A in real time; if M>D, executing step S300; if M<=D, continuing to execute step S200; wherein D is the first infusion mass of the basic drug set in medicine; and S300: sending a second infusion instruction to the driving structure to drive the upper branch tube B to start the infusion while prohibiting infusion in the upper branch tube A.

Optionally, it further includes the following steps:

S400: receiving detection data sent by the upper branch tube bubble detection device to which the upper branch tube B belongs in real time, and executing step S500 when the upper branch tube B is determined to have completed the infusion based on the received detection data; otherwise, continuing to execute step S400;

S500: sending a first infusion instruction to the driving structure to drive the upper branch tube A to start the infusion while prohibiting infusion in the upper branch tube B; and S600: receiving detection data sent by the upper branch tube bubble detection device to which the upper branch tube A belongs in real time, and controlling the upper branch tube A to stop the infusion when the upper branch tube A is determined to have completed the infusion based on the received detection data; otherwise, continuing to execute step S600.

The multi-channel automatic infusion pump provided by an embodiment of the present invention automatically controls the liquid passing and stopping operations of a plurality of channels through a multi-channel switching mechanism, and can automatically complete an automatic infusion operation of at least two bags of liquid medicine after one access. No medical staff operation is required during normal infusion process, medical staff can easily manage, save time and effort, and the risk of many uncertain factors can be reduced.

DETAILED DESCRIPTION

In order to make the technical problems, technical solutions and advantages to be solved by the present invention clearer, a detailed description will be given below in conjunction with the accompanying drawings and specific examples.

As shown in FIGS. 1, 9 to 11, an example of the present invention provides a multi-channel automatic infusion pump, including: a pump body 2, a pump door 3, an infusion switching mechanism, an exhaust device 16 and a bubble detection device which are provided on the pump body 2.

Figure 1:
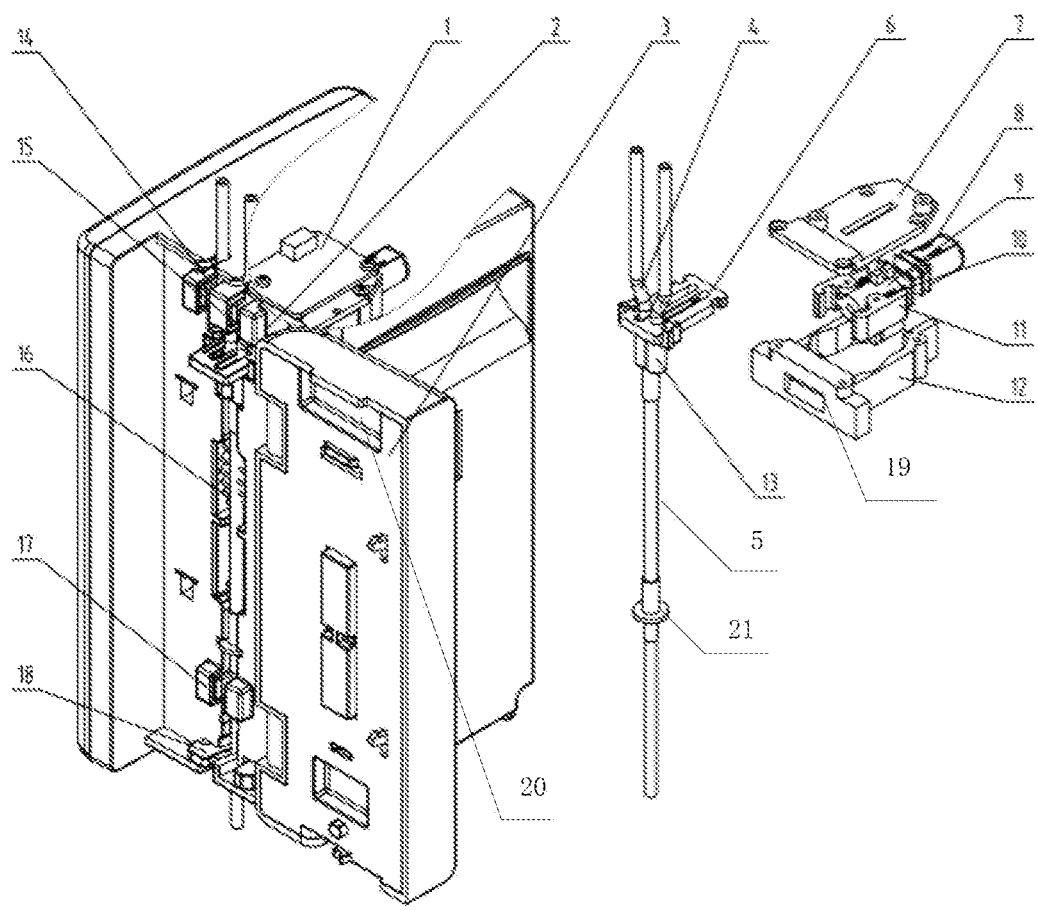
FIG. 1 is a schematic structural diagram of a multi-channel automatic infusion pump provided by an example of the present invention.

An installation space is formed inside the pump body 2, and an installation panel 14 is formed at the front end of the pump body 2. The pump door 3 and the installation panel 14 are movably connected with open or close the installation panel 14; the installation panel 14 is connected with the infusion consumable to form a placement slot for the infusion consumable. In an example of the present invention, the infusion consumable may include a multi-way connection joint, a plurality of upper branch tubes 4 (two upper branch tubes are shown in FIG. 1) and one main tube respectively connected with both ends of the multi-way connection joint 5. The multi-way connection joint includes N branch tube joints and 1 main tube joint connected with N branch tube joints, wherein N≥2. Correspondingly, the placement slot may include N connected upper branch tube placement slots, a multi-way connection joint placement slot and a main tube placement slot. The infusion consumables also include other consumables respectively connected with the upper branch tubes and the main tube. This part belongs to the existing structure and does not belong to the focus of the present invention. Therefore, for the sake of brevity, detailed descriptions of them are omitted.

Figure 2:
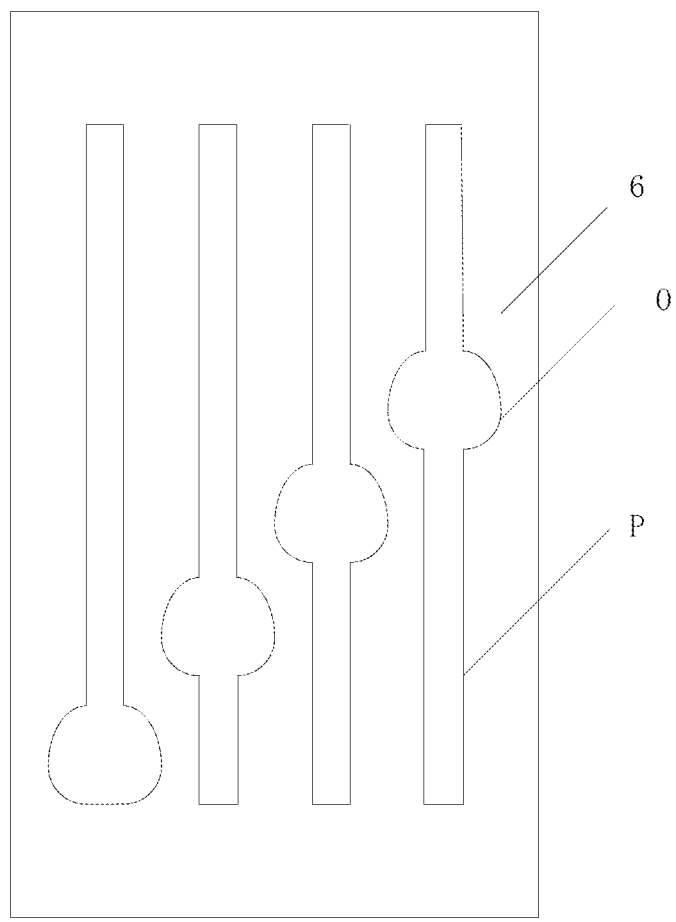
FIGS. 2 and 3 are structural schematic diagrams of a dual-channel infusion tube clamp according to an example of the present invention.

The infusion switching mechanism includes a multi-channel liquid-stopping clamp 6, a liquid-stopping clamp fixing base 12 and a driving structure. The liquid-stopping clamp fixing base 12 is fixed on the installation panel 14, and the front end of the liquid-stopping clamp fixing base is provided with an insertion slot 19 into which the multi-channel liquid-stopping clamp is inserted, the pump door is provided with a sliding slot 20 for the multi-channel liquid-stopping clamp to slide, and the insertion slot and the sliding slot cooperate to form a sliding channel; the multi-channel liquid-stopping clamp 6 includes a body and N channels formed on the body. As shown in FIG. 2, each channel includes a liquid-passing section O and a liquid-stopping section P. The liquid-passing section and the liquid-stopping section on each channel are set as: during the infusion process, when any one of the a plurality of upper branch tubes is located in the liquid-passing section of the corresponding channel, the other upper branch tubes are located in the liquid-stopping section of the corresponding channel, that is, when one of the infusion channels formed by a plurality of upper branch tubes and a main tube conducts the infusion, the other infusion channels are in a liquid-stopping state.

The driving structure is arranged at the upper end of the pump body, movably connected with the multi-channel liquid-stopping clamp, and is used to drive the multi-channel liquid-stopping clamp to move back and forth along the sliding channel, in order to make the upper branch tube selectively connected with the main tube.

The exhaust device is used to squeeze the main tube to exhaust air in the main tube. The bubble detection device is arranged on the installation panel and includes N upper branch tube bubble detection devices 15 and one main tube bubble detection device 17.

In an exemplary example of the present invention, the width of the liquid-stopping section of each channel of the multi-channel liquid-stopping clamp 6 is smaller than the diameter of the upper branch tube 4, and the specific width of which is arranged to be able to clamp the upper branch tube so that the upper branch tube is squeezed and deformed to prevent the upper branch tube from infusion. The liquid-passing section of each channel can be set to any shape and size, as long as it does not clamp the upper branch tube to enable normal infusion of the upper branch tube. In an exemplary example, the multi-channel liquid-stopping clamp 6 may include two channels, such as the dual-channel liquid-stopping clamp shown in FIG. 3, and one channel of the dual-channel liquid-stopping clamp shown in FIG. 3 includes two liquid-passing section. In the case that the multi-channel liquid-stopping clamp is double-channel, the multi-way connection joint may be a three-way connection joint.

Figure 9:
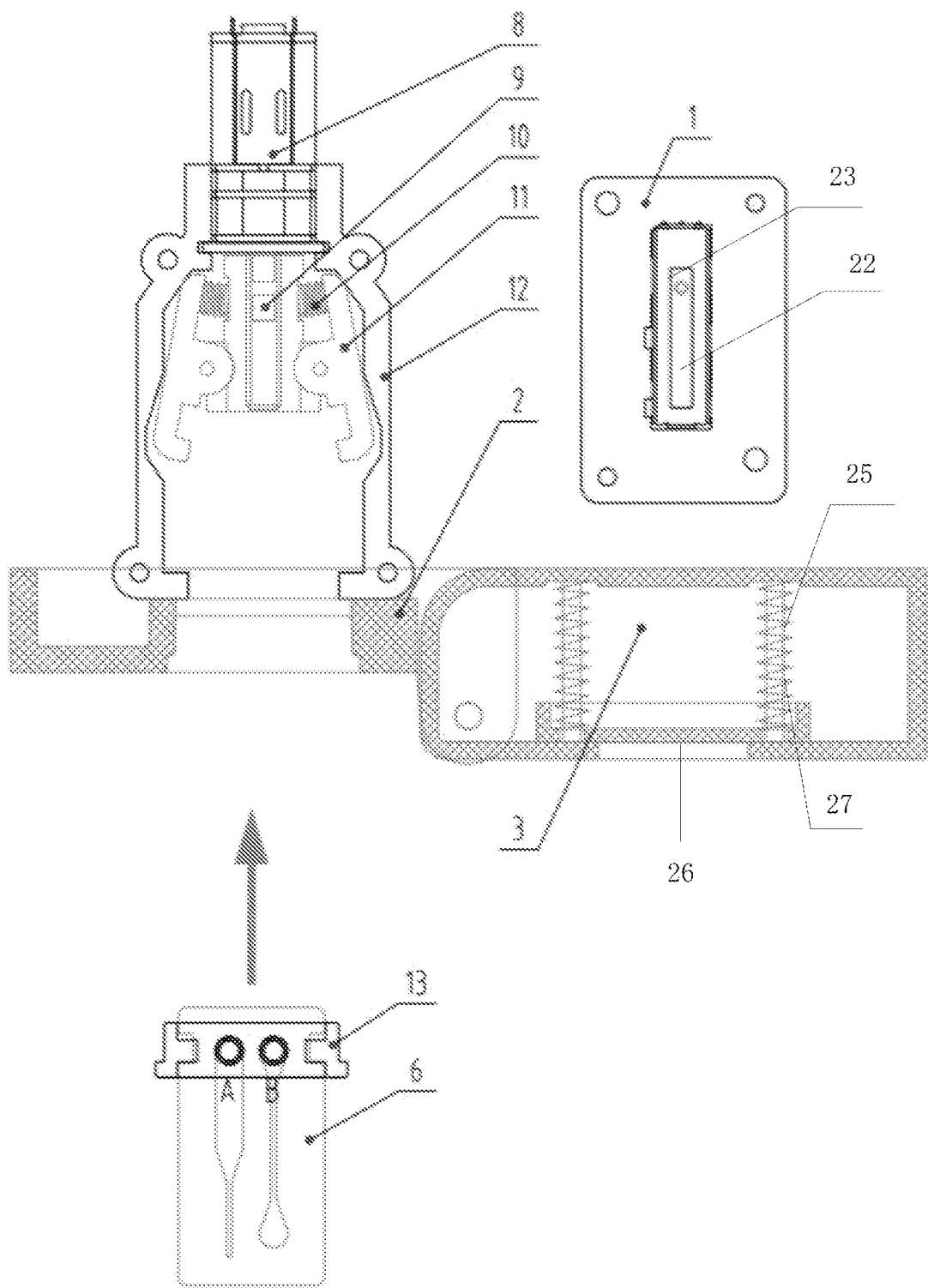
FIGS. 9 to 11 are diagrams showing the working principle of the multi-channel automatic infusion pump of the present invention.

Further, in an example of the present invention, the infusion switching mechanism further includes a detection plate 1 arranged above the driving structure. As shown in FIG. 9, the detection plate 1 is provided with a sliding rheostat 22, the driving structure is provided with a position detection point, and the sliding contact 23 of the sliding rheostat is ganged-linked to the position detection point 24.

Further, the driving structure may include a motor 8; and a push rod 9, a push rod attachment arm 11 and a spring 10 arranged in the liquid-stopping clamp fixing base. The motor 8 is connected with the rear end of the liquid-stopping clamp fixing base 12, the push rod 9 is connected with the motor 8, the push rod attachment arm 11 is movably arranged on both sides of the push rod 9, the spring 10 is arranged between the rear end of the push rod attachment arm 11 and the push rod 9, and the front end of the push rod attachment arm 11 is formed with a bent part; the multi-channel liquid-stopping clamp is formed with a recessed part that matches the bent part; the insertion slot 19 is arranged such that under the drive of the motor, the push rod attachment arm can be selectively combined with and separated from the multi-channel liquid-stopping clamp; and the position detection point 24 is arranged on the push rod 19.

Specifically, in an example of the present invention, a liquid-stopping clamp upper cover 7 is provided on the liquid-stopping clamp fixing base 12, and a detection plate 1 can be arranged on the liquid-stopping clamp upper cover 7. The liquid-stopping clamp upper cover 7 is provided with a strip slot for sliding the movable contact of the sliding rheostat. The push rod 9 can be a nut block, which is connected with the drive shaft of the motor 8 through a connecting structure. When the motor 8 drives the push rod 9 to move, the movable contact will move with the push rod. By detecting the change of the position detection point, the passing-stopping status of each upper branch tube can be determined so that the user can master the operation of the infusion pump. In specific applications, the push rod 9 can be arranged to have a preset length L, and the sliding rheostat of the detection plate 1 has a corresponding length L. Each time the push rod 9 moves forward or backward a preset distance, such as the distance between two adjacent liquid-passing sections, it represents channel switching for once. Correspondingly, when the push rod 9 moves to different positions, the sliding rheostat 22 can have different resistance values. Therefore, by monitoring the resistance value of the sliding rheostat 22 of the detection plate 1, the position of the motor 8 can be determined and then whether each branch tube is located in the corresponding position (the liquid-stopping section or the liquid-passing section) can be determined, that is, the passing-stopping status of each branch tube can be automatically identified, allowing users to easily master the operation of the infusion pump.

In addition, the spring 10 can be clamped between the push rod 9 and the push rod attachment arm 11 through a limiting slot. A first bent section, a second bent section and a straight section symmetrically arranged may be formed inside the insertion slot 19, and the maximum distance between the two first bent sections is smaller than the maximum distance between the two second bent sections. When the push rod attachment arm 11 is in the area formed by the first bent section and the second bent section, it can be in an open state due to the action of the spring. When the push rod attachment arm 11 is in the area formed by the straight section, it can be in a tightened state due to the action of the spring, that is, the push rod attachment arm 11 can be in a tight state for one stroke and an open state for the other stroke within the stop clamp fixing base 12.

In an example of the present invention, in an example of the present invention, the exhaust device may be a peristaltic pump 16. The peristaltic pump 16 is arranged in the installation space. The peristaltic pump 16 can be of an existing structure, that is, it includes a motor, an eccentric camshaft connected with the motor, and a plurality of shift fork pieces connected with the eccentric camshaft, wherein the plurality of shift fork pieces are connected with the main tube and are used for squeezing the main tube to exhaust air in the main tube under the driving action of the motor. The number of shift fork pieces can be arranged to 12, and an arc-shaped opening for the main tube 5 is formed on the shift fork pieces. The height of the shift fork pieces can be arranged to be different. When the main tube 5 is placed in the main tube placement slot, the main tube 5 will be inserted into the arc-shaped opening to connect with a plurality of shift fork pieces and drives the camshaft to rotate under the action of the motor of the peristaltic pump 6. With the rotation of the camshaft, each shift fork piece moves forward and backward in sinusoidal waveform state, that is because the two highest shift fork pieces squeeze and contact the infusion tube to form a section of closed liquid, and then through the high and low switching of each shift fork piece, the closed liquid will be squeezed and pushed forward to achieve exhaust of the main tube.

In addition, a two-way connection joint 21 is provided on the main tube. The two-way connection joint 21 is arranged below the extrusion section, and may include a circular support platform and connecting tubes connected with both ends of the circular support platform, and a slot for inserting the circular support platform is formed on the main tube placement slot. In this way, since the two ends of the main tube are respectively connected with a multi-way connection joint and a two-way connection joint, it can be firmly fixed in the extrusion section, which can avoid the influence of the movement of the shift fork piece on the accuracy of the infusion and the influence on the bubble detection device at the lower end.

In an example of the present invention, the part of the main tube in contact with the shift fork piece is made of silica gel. Due to the use of silicone tube, it has more resilience and resilience than the conventional PVC tube, and can ensure long-term infusion accuracy. The silicone tube is connected with a multi-way connection joint at one end, which can be fixed and cooperated with a multi-channel liquid-stopping clamp to realize a state switch between infusion tubes and is also convenient for medical staff to install and operate.

In an example of the present invention, the upper branch tube bubble detection device 15 and the main tube bubble detection device 17 may be bubble sensors, which are used to detect bubbles in the corresponding infusion tube to determine whether the infusion tube is blocked or empty. Each upper branch tube bubble detection device 15 may be arranged on the side of the lower end of the corresponding upper branch tube, and the main tube bubble detection device 17 may be arranged on the side of the lower end of the main tube.

Further, in an example of the present invention, as shown in FIG. 9, the sliding slot 20 may be provided with an elastic support structure in contact with the multi-channel liquid-stopping clamp, wherein the elastic support structure may include two connecting rods 25 and a supporting plate 26 movably connected with the two connecting rods 25, a spring 27 is arranged between the supporting plate 26 and the connecting rod 25, that is, the spring 27 is sleeved on the connecting rod. Through the elastic support structure, when the infusion pump is working, the multi-channel liquid-stopping clamp can be gently pressed, which is beneficial to stabilize the position of the multi-channel liquid-stopping clamp and has the effect of preventing the entry of dirt and debris.

Further, in an example of the present invention, it further includes a mechanical liquid-stopping clamp 18, which is arranged at the lower end of the pump body and is used to cooperate with the pump door 3 so that the main tube is in a liquid-passing state or liquid-stopping state. In an example of the present invention, the mechanical liquid-stopping clamp 18 may be an existing mechanical liquid-stopping clamp. In a preferred example, as shown in FIGS. 4 to 7, the mechanical liquid-stopping clamp 18 may include: a mechanical liquid-stopping clamp fixing base 28; a liquid-stopping knife clamp 29, a knife clamp spring 30, a liquid-stopping push rod 31 and a push rod spring 32 arranged on the mechanical liquid-stopping clamp fixing base 28. The front end of the liquid-stopping push rod 31 extends out of the installation panel 2 through the front end of the mechanical liquid-stopping clamp fixing base, and the rear end is connected with that of the mechanical liquid-stopping clamp fixing base through the push rod spring 32; the liquid-stopping knife clamp 29 may include a liquid-stopping portion and a connecting portion connected by a connecting shaft, wherein the connecting portion is movably connected with the rear end of the liquid-stopping push rod, and the front end of the liquid-stopping portion is formed with a bent part 33, the pump door is formed with a limiting slot 34 adapted to the bent part; the knife clamp spring is arranged between the rear end of the liquid-stopping part and the mechanical stop clamp fixing base. The rear end of the liquid-stopping push rod is formed with a hook 35 hooking the connecting part, by which the movable connection of the liquid-stopping push rod and the liquid-stopping knife clamp can be realized. The knife clamp spring 30 may include a spirally formed spring body and two straight torsion arms extending along both ends of the spring body. The spring body is sleeved on the rotating shaft, and the two straight torsion arms are respectively respectively in abutting contact with the liquid-stopping knife clamp and the mechanical liquid-stopping knife clamp fixing base.

In an example of the present invention, the liquid-stopping push rod and the liquid-stopping knife clamp are set such that the thrust of the liquid-stopping push rod on the pump door F1 is ≤0.1 N; the pressure of the liquid-stopping knife clamp on the pump door is ≈15 N, and the force direction is downward, so as to effectively reduce the risk of pump door deformation.

In an example of the present invention, the multi-channel automatic infusion pump further includes a controller (not shown). The driving structure, the exhaust device and the bubble detection device are all communicatively connected with the controller and execute corresponding operations based on the instructions of the controller. In addition, the sliding rheostat of the detection plate 1 is also connected with the controller. The resistance value of the sliding rheostat can be sent to the controller in real time. The controller can determine the position of the motor of the driving structure according to the received resistance value, and then according to the stored positional relationship of the liquid-stopping section of each channel of the multi-channel liquid-stopping clamp, the position of each branch tube can be known, so that the passing-stopping status of each branch tube can be known to ensure that each branch tube can be accurately located in the corresponding position. The multi-channel automatic infusion pump of the example of the present invention can execute corresponding infusion operations based on the control of the controller.

In an example of the present invention, when two or more channels $C_1, C_2 \ldots C_N$ need to be used for infusion, the drive structure can be controlled to drive the multi-channel liquid-stopping clamp to move outwards according to the arrangement sequence of the upper branch tube installed in the channel liquid-stopping clamp (in the invention it is arranged from left to right, namely $C_1, C_2 \ldots C_N$). Then the drive structure drives the multi-channel liquid-stopping clamp to move inward so that the upper branch tube infused sequentially in reverse order $C_N, \ldots, C_2, C_1$ successively, so as to minimize the driving stroke of the motor.

Figure 3:
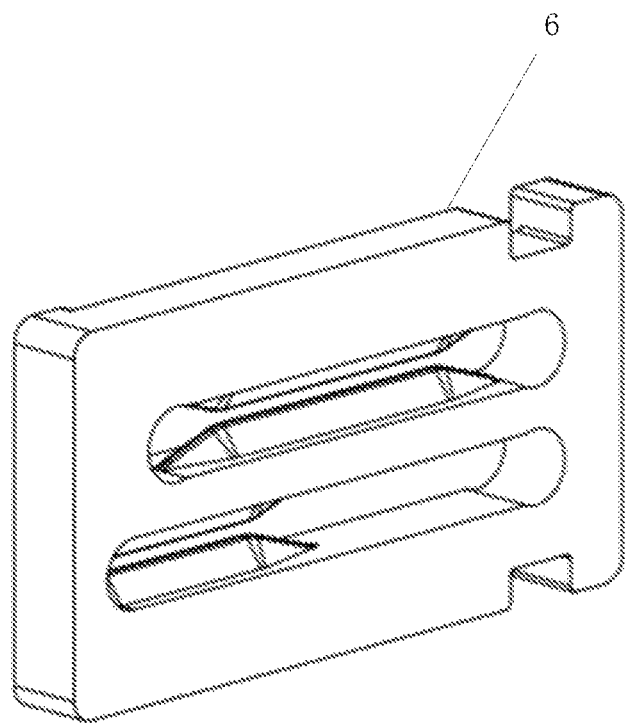
Figure 4:
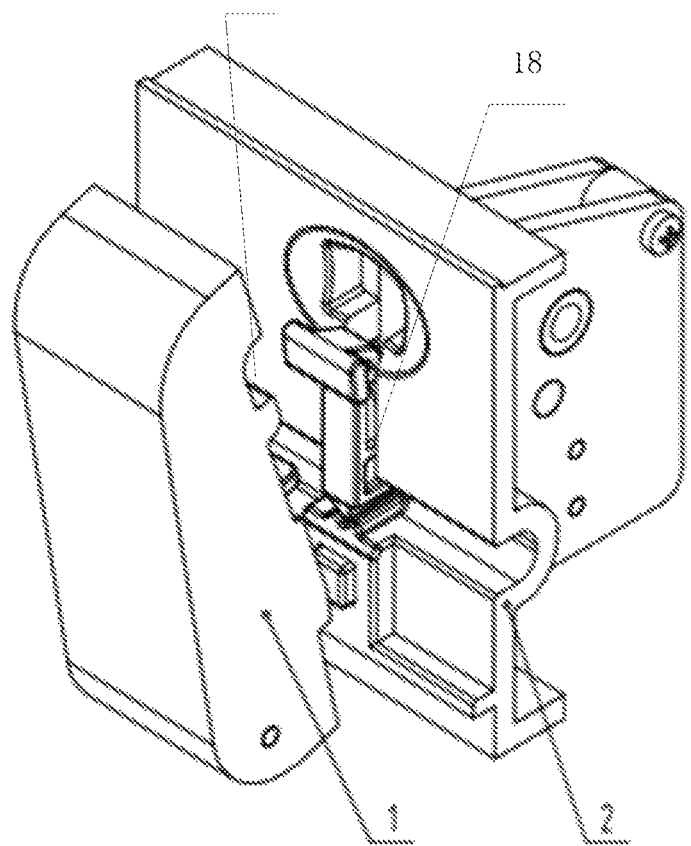
FIGS. 4 and 5 are structural schematic diagrams of a mechanical liquid-stopping clamp of a multi-channel automatic infusion pump according to an example of the present invention.
Figure 5:
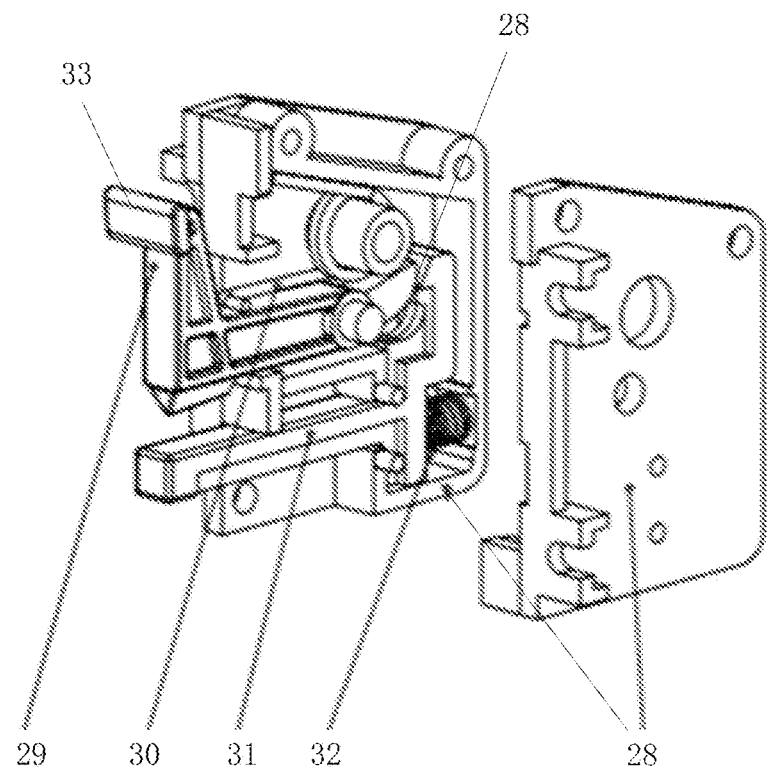

In another example of the present invention, for dual-channel infusion, reverse exhaust can also be performed first, followed by positive infusion. In this example, the multi-way connection joint is a three-way connection joint, and the channel on the right side of the multi-channel liquid-stopping clamp 6 is formed with two liquid-passing sections at both ends. As shown in FIG. 3, the automatic infusion pump performs the infusion according to the steps of the reverse exhaust first and then positive infusion.

Figure 6:
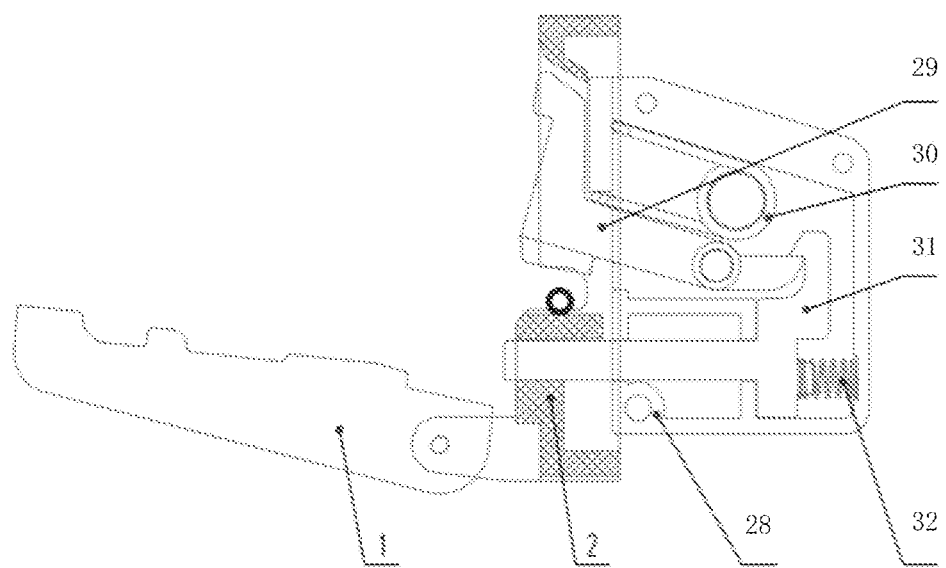
FIGS. 6 and 7 are diagrams of the working principle of the mechanical liquid-stopping clamp.

Referring to FIGS. 6 and 7 and FIGS. 9 to 11, the method of using the multi-channel automatic infusion pump of the present invention for dual-channel infusion will be introduced hereinafter. The method of using the automatic infusion pump of the present invention for dual-channel infusion includes the following steps:

1. Installation of Infusion Consumables:

The pump door 3 is opened, and the infusion set with the infusion tube clamp 6 is installed. The upper branch tube, the three-way connection joint, and the main tube of the infusion consumables are placed on the corresponding placement slots on the installation panel. When installing the main tube, the liquid-stopping knife clamp 29 of the mechanical liquid-stopping clamp 18 is pressed to the end and released. During this process, the liquid-stopping push rod 31 is pushed backward first, and then under the action of the push rod spring 32, it resets and hooks the liquid-stopping knife clamp 29, then can be loaded into the main tube 5, as shown in FIG. 6.

After the infusion consumable is fixed to the installation panel 14, as shown in FIG. 9, the two infusion channels A and B of the infusion consumable which are formed by the two upper branch tubes 15 and the main tube 5 are in the initial state of opening. During the process of inserting the multi-channel liquid-stopping clamp 6 along the insertion slot to the end, since the blocking of the three-way connection joint 13 and the installation panel 2 of the infusion pump, the infusion tube relatively moves to the lower end position of the channel of the liquid-stopping clamp 6, that is, the infusion channel B is in the state of conduction. Then the dripping pots corresponding to the two infusion channels are manually squeezed to fill a certain amount of liquid.

2. Automatic Emptying:

2.1: After closing the pump door and self-checking, the emptying operation is chosed to enter: after the peristaltic pump 16 is started, the infusion channel B will run to exhaust under the action of the pump pressure because the infusion channel B is unblocked.

In the process of pump door closing, the state of the mechanical liquid-stopping clamp 18 is as follows:

(1) When the pump door is closed to a certain distance, the pump door will come into contact with the liquid-stopping push rod 31, and the liquid-stopping push rod will be triggered to retreat, so that the liquid-stopping knife clamp 29 is disconnected from it. Under the action of the knife clamp spring 30, the liquid-stopping knife clamp 29 drops first until it hits the pump door.

Figure 7:
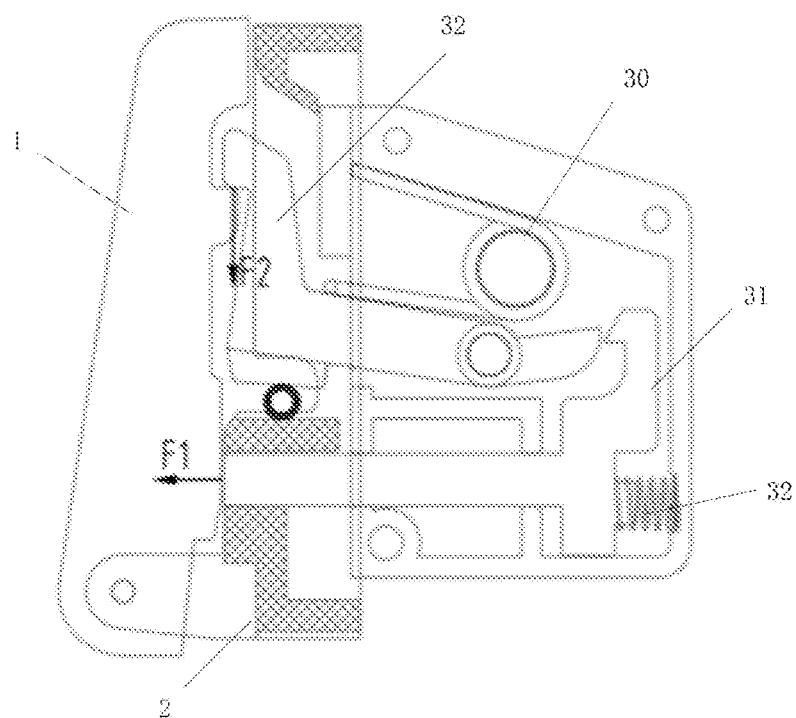

(2) The pump door is continued to be closed while lifting the liquid-stopping knife clamp 29 until the front end of the liquid-stopping knife clamp 29 slides into the limiting slot of the pump door. After the pump door is completely closed, normal infusion operations are executed. At this time, the liquid-stopping push rod 31 remains unhooked, and the consumable tube where the liquid-stopping knife clamp 29 is located remains unblocked, as shown in FIG. 7.

Figure 10:
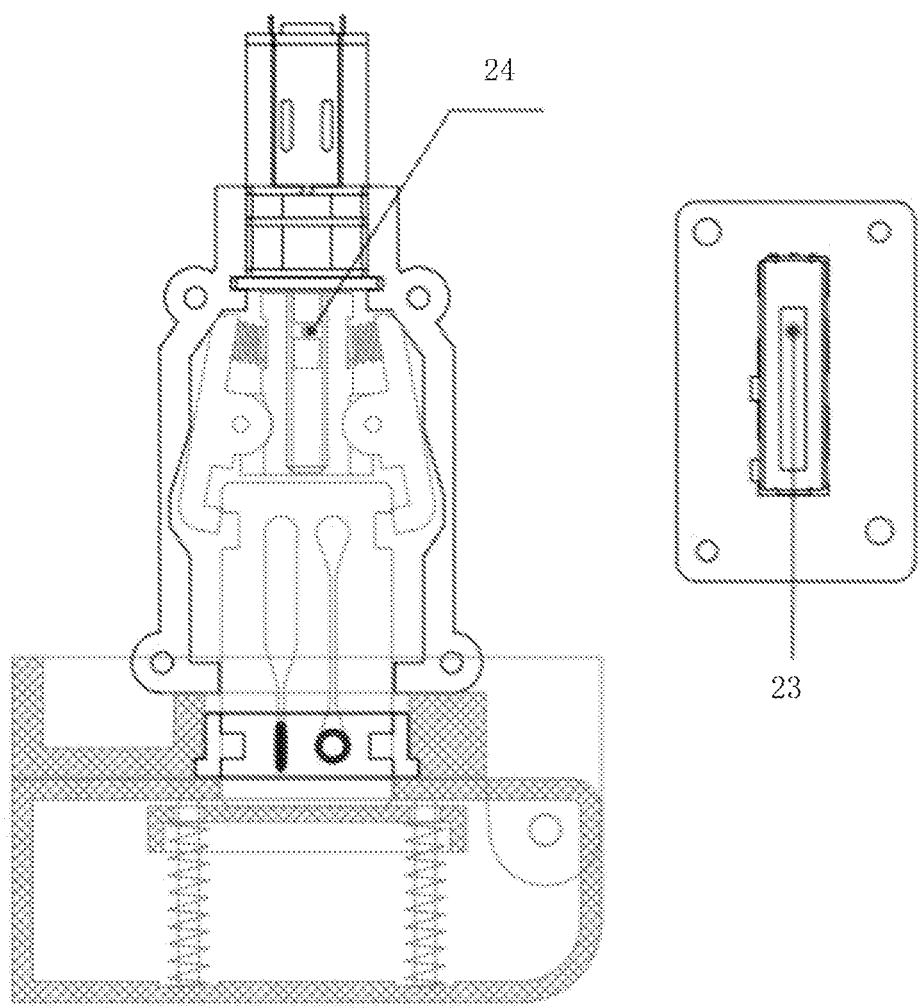

2.2: When the upper branch tube bubble detection device for detecting the infusion channel B determines that there is no bubble and the delay, the peristaltic pump 16 first stops running, and the motor 8 is turned on, driving the push rod nut block 9 to move forward. At this time, the push rod attachment arm and the liquid-stopping clamp 6 are combined together, and push liquid-stopping clamp 6 out for a certain distance under the push of the push rod nut block. Because of the blocking of the three-way connection joint 13 and the pump door 3, the infusion tube remains in place, that is, the infusion tube moves relatively to the middle end of the tube clamp, and enters the working state where the infusion channel A is conductive, and then the peristaltic pump 16 continues to run to execute the exhaust action of the infusion channel A, as shown in FIG. 10.

2.3: When the bubble detection device for detecting the infusion channel A determines that there are no bubbles, that is, after both the upper branch tube bubble detection device and the main tube bubble detection device determine that there are no bubbles, the emptying is completed.

Figure 11:
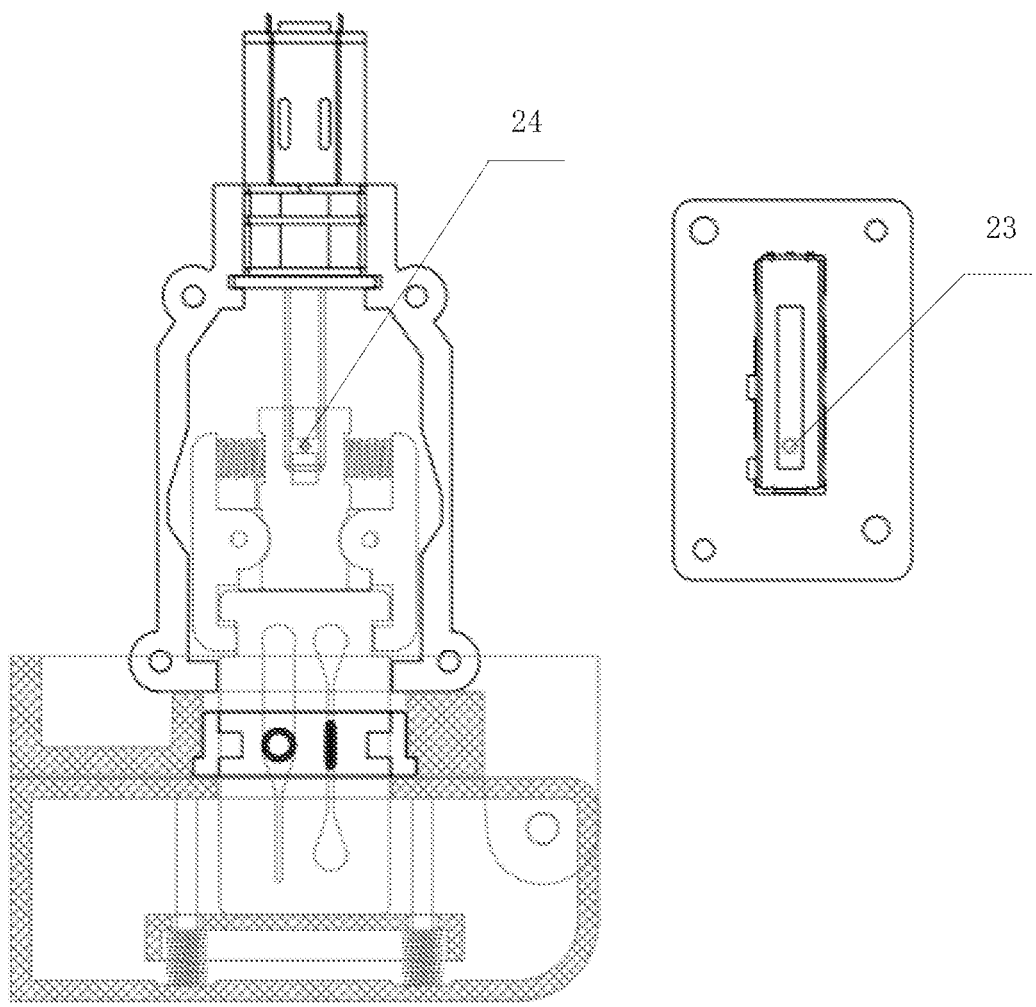

3. Operation of the infusion:

3.1: The infusion channel A executes the infusion operation first. When the bubble detection device determines that there are bubbles in the infusion channel A, the peristaltic pump 16 immediately stops running, and then the motor 8 runs in reverse and pulls the liquid-stopping clamp 6 back to the original position through the action of the push rod nut block 9 and the push rod attachment arms 11 on both sides, thereby switching to the working state that the infusion channel B is conductive, as shown in FIG. 11;

3.2: Subsequently, the peristaltic pump 16 continues to operate to achieve the infusion of the infusion channel B. When the bubble detection device determines that the infusion channel B has bubbles, the peristaltic pump 16 stops running and the infusion is completed.

4. Removal of the infusion consumables:

4.1: When the pump door is opened, the motor 8 will first pull back the liquid-stopping clamp 6 through the push rod nut block 9 and the push rod attachment arms 11 on both sides, and finally the rear end of the push rod attachment arm 11 is constrained by the structure of the liquid-stopping clamp fixing base 12, the claws at the front ends of the two attachment arms open by themselves. At this time, the consumables with the liquid-stopping clamp 6 can be removed, as shown in FIG. 3;

In the process of opening the pump door, the state of the mechanical liquid-stopping clamp 18 is as follows:

Because in the infusion process, the liquid-stopping push rod 31 is in an unhooked state, under the action of the knife clamp spring 30, once the pump door 3 opens for a little angle, the front end of the liquid-stopping knife clamp 29 is separated from the limiting slot of the pump door and falls quickly, the main tube will prevent the liquid from passing after being squeezed and deformed. After the pump door is fully opened, the infusion consumables can be simply pulled out.

4.2: If the consumables are temporarily removed during the infusion process, after reinstallation and restart, the infusion pump can first self-check the status of each bubble detection device to determine the current process status, and at the same time, it will ask whether to choose to empty or enter the next step.

4.3: If there is no need to remove the tube, the pump door can be closed directly, and the system will reset the motor 8 to the state before opening the door according to the memory information before the operation was interrupted, and prompt the next operation.

However, there is a special infusion situation in medicine. In this case, it is necessary to input a certain mass/volume (hereinafter referred to as mass, and those skilled in the art can understand that mass and volume are equivalent) of basic drug X, and then the increased treatment drug Y, and then the basic drug X. In this case, the three channels in the foregoing example can be used, that is, the first channel corresponds to the corresponding mass of the basic drug X (called X1), the second channel corresponds to the added therapeutic drug Y, and the third channel also corresponds to the basic drug X (called X3). However, in some cases, the automatic infusion pump only has two channels, or the basic drug X input medically is already the smallest packaging unit and cannot be divided into two parts X1 and X3.

In order to solve the above technical problem, in another example of the present invention, the controller is used to control the driving structure to drive the multi-channel liquid-stopping clamp so as to make the two adjacent upper branch tubes perform infusion according to a preset infusion mode. The preset infusion method includes: controlling one of the two adjacent upper branch tubes to transport a preset mass of liquid first, and then controlling the other upper branch tube to infuse the fluid, and after the other upper branch tube has completed the infusion, controlling the upper branch tube that was infused first to continue the infusion.

Specifically, for the two adjacent upper branch tubes A and B, when the infusion of the upper branch tube A is the basic drug and the infusion of the upper branch tube B is the added therapeutic drug, the controller executes a control instruction to achieve the following steps:

S100: sending a first infusion instruction to the driving structure to drive the upper branch tube A to start the infusion while prohibiting infusion in the upper branch tube B;

S200: acquiring the infusion mass M of the upper branch tube A in real time; if M>D, executing step S300; if M≤D, continuing to execute step S200; wherein D is the first infusion mass of the basic drug set in medicine; and S300: sending a second infusion instruction to the driving structure to drive the upper branch tube B to start the infusion while prohibiting infusion in the upper branch tube A.

Further, it also includes the following steps:

S400: receiving detection data sent by the upper branch tube bubble detection device to which the upper branch tube B belongs in real time, and executing step S500 when the upper branch tube B is determined to have completed the infusion based on the received detection data; otherwise, continuing to execute step S400;

In this step, the bubble detection device to which the upper branch tube B belongs detects the bubbles in the upper branch tube B in real time, and sends the detected detection data to the controller, wherein the values 0 and 1 can be used to indicate the detection of bubbles and no bubbles. Based on the received detection data, the controller determines whether the upper branch tube B has completed the infusion. When the controller receives the detection data that characterizes the detection of bubbles, it determines that the upper branch tube B has completed the infusion, and then executes step S500; otherwise, it determines that the upper branch tube B has not completed the infusion, then continue to execute step S400;

S500: sending a first infusion instruction to the driving structure to drive the upper branch tube A to start the infusion while prohibiting infusion in the upper branch tube B; and S600: receiving detection data sent by the upper branch tube bubble detection device to which the upper branch tube A belongs in real time, and controlling the drive structure to drive the upper branch tube A to stop the infusion when the upper branch tube A is determined to have completed the infusion based on the received detection data; otherwise, continuing to execute step S600.

In this step, the bubble detection device to which the upper branch tube A belongs detects the bubbles in the upper branch tube A in real time, and sends the detected detection data to the controller, wherein the values 0 and 1 can be used to indicate the detection of bubbles and no bubbles. Based on the received detection data, the controller determines whether the upper branch tube A has completed the infusion. When the controller receives the detection data that characterizes the detection of bubbles, it determines that the upper branch tube A has completed the infusion, and then the driving structure is controlled to drive the movement of the multi-channel liquid-stopping clamp so that the upper branch pipe A is in the liquid-stopping section to stop the infusion thereby completing the infusion operation; otherwise, it is determined that the upper branch tube A has not completed the infusion, then continue to execute step S600.

Figure 8:
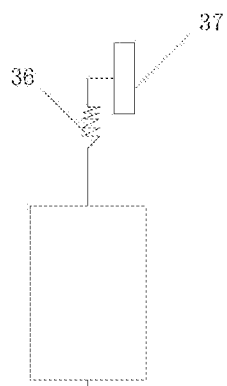
FIG. 8 is a schematic structural diagram of the infusion monitoring device of the present invention.

In one example (Example 1), as shown in FIG. 8, the automatic infusion pump further includes an infusion monitoring device, which is communicatively connected with the controller, and can include a spring 36 and a sliding rheostat 37, wherein one end of the spring 36 is connected with an infusion bag connected with the upper branch tube, and the other end is connected with a sliding contact of the sliding rheostat 37; and the infusion mass M can be determined according to the resistance value of the associated sliding rheostat. For example, when the infusion bag contains 500 grams of solution, the sliding rheostat has the first resistance value R1, and when the infusion is halfway through and 250 grams of solution remain, the sliding rheostat has the second resistance value R2, in this way, the mass of the infusion can be obtained according to the first resistance value R1 and the second resistance value R2.

In another example (Example 2), the automatic infusion pump further includes a timer, which is communicatively connected with the controller for acquiring the dripping time of the upper branch tube. The infusion mass M is determined according to the dripping time acquired by the timer, that is, the timer value (second), and the preset dripping speed (g/sec), for example, M=timer value*dripping speed.

Following the previous two examples, in a further example (Example 3), the step S200 further includes:

S210: acquiring the first infusion mass M1 according to the infusion monitoring device;

S220: acquiring the second infusion mass M2 according to the timer value and the preset dripping speed; and S230: if |M1−M2|/max(M1, M2)>D1, issuing an early warning message; otherwise, setting M=M1; wherein D1 is the absolute value of the infusion dripping speed error threshold corresponding to the upper branch tube A, and the dripping velocity error threshold can be set according to actual conditions.

When determining the mass of infusion, (1) if only M1 is used, there may be inaccuracies caused by spring or sliding rheostat aging or malfunction; (2) If only M2 is used, manual dripping rate adjustment errors may occur. Therefore, determining the mass of the infusion based on M1 and M2, namely step S230, can solve the aforementioned problems (1) and (3). In addition, since M1 will become more reliable, it is preferable to use M1 as M when M1 and M2 are within the error range, which is more accurate.

Further, in step S230, alternatively, M=(M1+M2)/2 is set.

In an example of the present invention, the relevant software code used in the controller includes:

---

1. Software Interface
Control Motor Interface Pins:
PA_Pin_5----->POWER_VERF
PB_Pin_0----->AD
PB_Pin_7----->DIR
PB_Pin_8----->STEP
PB_Pin_10----->POWER
2. Data Type 1
define MOTOR_SW_DIR PBout(7)
define MOTOR_SW_STEP PBout(8)
define MOTOR_SW_EN PBout(10)
3. Data Type 2
typedef enum {
CHANNEL_A_OPEN,
CHANNEL_B_OPEN,
CHANNEL_AB_OPEN,
}CHANNEL_KIND;
4. Function Interface
/*Interface initialization*/
void Channel_Switch_Init( );
void DAC_Configuration( );
void Adc_Init(void);
/*Channel switching interface*/
void Channel_Switch(CHANNEL_KIND kind);
Function Interface Detailed Design
void Channel_Switch_Init(void)
{
  GPIO_InitTypeDef GPIO_InitStructure;
  RCC_APB2PeriphClockCmd(RCC_APB2Periph_GPIOB, ENABLE);
  GPIO_InitStructure.GPIO_Pin=GPIO_Pin_7|GPIO_Pin_8|GPIO_Pin_10;
  GPIO_InitStructure.GPIO_Mode=GPIO_Mode_Out_PP;
  GPIO_InitStructure.GPIO_Speed=GPIO_Speed_50MHz;
  GPIO_Init(GPIOB,&GPIO_InitStructure);
}
void DAC_Configuration(void)
{
  DAC_InitTypeDef DAC_InitStructure;
  GPIO_InitTypeDef GPIO_InitStructure;
RCC_APB2PeriphClockCmd( RCC_APB2Periph_GPIOA, ENABLE);
  GPIO_InitStructure.GPIO_Pin = GPIO_Pin_4|GPIO_Pin_5;
  GPIO_InitStructure.GPIO_Mode = GPIO_Mode_AIN;

```
    GPIO_InitStructure.GPIO_Speed = GPIO_Speed_50MHz;
    GPIO_Init(GPIOA, &GPIO_InitStructure);
    DAC_DeInit( );
    RCC_APB1PeriphClockCmd(RCC_APB1Periph_DAC, ENABLE);
    DAC_InitStructure.DAC_Trigger = DAC_Trigger_None;
    DAC_InitStructure.DAC_WaveGeneration = DAC_WaveGeneration_
None;
    DAC_InitStructure.DAC_OutputBuffer = DAC_OutputBuffer_Enable;
    DAC_InitStructure.DAC_LFSRUnmask_TriangleAmplitude &=0xfffef-
fff;
    DAC_Init(DAC_Channel_1, &DAC_InitStructure);
    DAC_DMACmd(DAC_Channel_1,DISABLE);
    DAC_Cmd(DAC_Channel_1, ENABLE);
    DAC_SoftwareTriggerCmd(DAC_Channel_1,ENABLE);
    DAC_Init(DAC_Channel_2, &DAC_InitStructure);
    DAC_DMACmd(DAC_Channel_2,DISABLE);
    DAC_Cmd(DAC_Channel_2, ENABLE);
    DAC_SoftwareTriggerCmd(DAC_Channel_2,ENABLE);
}
void Adc_Init(void)
{
    Adc_GPIO_Init( );
    /* DMA channel1 configuration --------------------------------------*/
    DMA_DeInit(DMA1_Channel1);
    DMA_InitStructure.DMA_PeripheralBaseAddr = ADC1_DR_Address;
    DMA_InitStructure.DMA_MemoryBaseAddr = (u32)ADC_Buf;
    DMA_InitStructure.DMA_DIR = DMA_DIR_PeripheralSRC;
    DMA_InitStructure.DMA_PeripheralInc = DMA_PeripheralInc_Disable;
    DMA_InitStructure.DMA_MemoryInc = DMA_MemoryInc_Enable;
    DMA_InitStructure.DMA_PeripheralDataSize =
DMA_PeripheralDataSize_HalfWord;
    DMA_InitStructure.DMA_MemoryDataSize =
DMA_MemoryDataSize_HalfWord;
    DMA_InitStructure.DMA_Mode = DMA_Mode_Circular;
    DMA_InitStructure.DMA_Priority = DMA_Priority_High;
    DMA_InitStructure.DMA_M2M = DMA_M2M_Disable;
    DMA_Init(DMA1_Channel1, &DMA_InitStructure);
    /* Enable DMA channel1 */
    DMA_Cmd(DMA1_Channel1, ENABLE);
    /* ADC1 configuration -----------------------------------------------*/
    ADC_InitStructure.ADC_Mode = ADC_Mode_Independent;
    ADC_InitStructure.ADC_ScanConvMode = ENABLE;
    ADC_InitStructure.ADC_ContinuousConvMode = ENABLE;
    ADC_InitStructure.ADC_ExternalTrigConv = ADC_ExternalTrigConv_
None;
    ADC_InitStructure.ADC_DataAlign = ADC_DataAlign_Right;
    ADC_InitStructure.ADC_NbrOfChannel = 4;
    ADC_Init(ADC1, &ADC_InitStructure);
    /* ADC1 regular channel14 configuration */
    ADC_RegularChannelConfig(ADC1, ADC_Channel_10, 5,
ADC_SampleTime_55Cycles5);
    ADC_RegularChannelConfig(ADC1, ADC_Channel_11, 2,
ADC_SampleTime_55Cycles5);
    ADC_RegularChannelConfig(ADC1, ADC_Channel_12, 3,
ADC_SampleTime_55Cycles5);
    ADC_RegularChannelConfig(ADC1, ADC_Channel_13, 4,
ADC_SampleTime_55Cycles5);
    ADC_RegularChannelConfig(ADC1, ADC_Channel_8, 1,
ADC_SampleTime_55Cycles5);
    /* Enable ADC1 DMA */
    ADC_DMACmd(ADC1, ENABLE);
    /* Enable ADC1 */
    ADC_Cmd(ADC1, ENABLE);
    /* Enable ADC1 reset calibaration register */
    ADC_ResetCalibration(ADC1);
    /* Check the end of ADC1 reset calibration register */
    while(ADC_GetResetCalibrationStatus(ADC1));
    /* Start ADC1 calibaration */
    ADC_StartCalibration(ADC1);
    /* Check the end of ADC1 calibration */
    while(ADC_GetCalibrationStatus(ADC1));
    /* Start ADC1 Software Conversion */
    ADC_SoftwareStartConvCmd(ADC1, ENABLE);
}
void Channel_Switch(CHANNEL_KIND kind)
{
    SYS_CORE_STRUCT_PTR sys_core_ptr = NULL;
    u16 times=0;
    u16 overtime=0;
    s16 temp;
    u16 chl_pos = 0;
    u8 dir_flag;
    uint16 chl2_Ref;
    chl2_Ref=(2.0*4096)/3.3;
    GET_SYS_CORE_DATA(sys_core_ptr);
    DAC_SetChannel2Data(DAC_Align_12b_R,chl2_Ref);
    DAC_SoftwareTriggerCmd(DAC_Channel_2,ENABLE);
    if(sys_core_ptr->SYS_STAT==SYS_STATE_CLAMP_SWITCH_ERR)
        goto END;
    switch(kind) {
        case CHANNEL_A_OPEN: {
            chl_pos = 1960;
        }break;
        case CHANNEL_B_OPEN: {
            chl_pos = 1800;
        }break;
        case CHANNEL_AB_OPEN: {
            chl_pos = 330;
        }break;
        default:
            return;
    }
    MOTOR_SW_EN=0;
    if (chl_pos > ADC_Buf[0]) {
        MOTOR_SW_DIR = 1;
        dir_flag = 0;
    }
    else {
        MOTOR_SW_DIR = 0;
        dir_flag = 1;
    }
    while(1) {
        while(times < 500) {
            MOTOR_SW_STEP = 1;
            delayUs(500);
            MOTOR_SW_STEP = 0;
            //delayUs(5000);
            times++;
        }
        times = 0;
        overtime++;
        if (overtime > 50000 || ((dir_flag == 0 && chl_pos < ADC_Buf[0]) ||
(dir_flag == 1 && chl_pos > ADC_Buf[0])))
            break;
    }
    END:
    MOTOR_SW_EN=1;
}
```

Furthermore, a long continuous infusion is required for some cases such as common pneumonia, which generally requires about 10 days of infusion. In this case, there is a need to maintain the relative droplet velocity of the infusion for each infusion.

In order to solve the above technical problem, in an example of the present invention, it further includes a server (not shown) communicatively connected with the controller, wherein the server stores a user ID and a historical infusion drop velocity vector (V1, V2, . . . , Vn) corresponding to the user ID, wherein $Vi=mi/ti$, mi is the mass of the infusion at the completion of the i-th infusion in the same infusion, ti is the dripping time obtained by the timer at the completion of the i-th infusion, and N is the historical number of infusion.

The controller and the server execute a computer program to implement the following steps:

S10: sending the first infusion mass M1 and the dripping time t obtained by the timer by the controller to the server every preset time T (for example, 5-10 minutes). The values of T and t are basically the same, but there may be a little error due to actual operation. Therefore, to ensure accuracy, the dripping time t is used in the present invention.

S20: acquiring the average dripping speed $V=M1/t$ corresponding to the preset time T by the server;

S30: if min(Vi≤V≤max(Vi), indicating that the dripping speed is within a reasonable range, no additional processing will be executed; otherwise, if V>max(Vi) or V<min(Vi), executing S40;

S40: if [max(Vi)−min(Vi)]/max(Vi)>D2, giving an early warning; otherwise, executing S50;

D2 can be determined according to the absolute value of the preset infusion dripping speed error threshold. Preferably, D2 is smaller than the absolute value of the error threshold, for example, D2 is between 0.05 and 0.1. The early warning can be carried out by means of voice prompts or other means, and the present invention is not particularly limited.

S50: if V>max(Vi) and [V−max(Vi)]/max(Vi)>D2, giving an early warning; or if V<min(Vi) and [min(Vi)−V]/V>D2, giving an early warning.

In this example, according to the historical dripping speed and the dripping speed in the current time T, it can be automatically determined whether the dripping speed is appropriate; in addition, in steps S30-S50, the judgment processing executed based on V, D2, and Vi can effectively prevent misjudgment when the historical drip data is small or relatively smooth.

In an alternative example of the present invention, it may include a plurality of infusion switching mechanisms. Each infusion switching mechanism is basically the same as that of the previous example, except that the liquid-stopping clamp only forms one channel. In this example, each liquid-stopping clamp can be controlled by a separate driving structure, that is, each infusion channel can be independently controlled, which can make the infusion operation more convenient.

In summary, the multi-channel automatic infusion pump provided by an example of the present invention automatically controls the liquid passing and stopping operations of a plurality of channels through a multi-channel switching mechanism, and can automatically complete a sequential infusion operation of at least two bags of liquid medicine after one access. No medical staff operation is required during normal infusion process, medical staff can easily manage, save time and effort, and the risk of many uncertain factors can be reduced.

The above-mentioned examples are only specific implementations of the present invention and are used for the illustration of the technical solution of the present invention, rather than a limitation, the protection scope of the present invention is not limited thereto. Although the present invention has been described in detail with reference to the foregoing examples, those of ordinary skill in the art should understand that any person skilled in the art can still modify or easily think of changes to the technical solutions described in the foregoing examples within the technical scope disclosed in the present invention, or equivalently replace some of the technical features; these modifications, changes or replacements do not deviate the essence of the corresponding technical solutions from the spirit and scope of the technical solutions of the examples of the present invention, and should be covered within the protection scope of the present invention. Therefore, the protection scope of the present invention should be subject to the protection scope of the claims.

The invention claimed is:

1. A multi-channel automatic infusion pump, comprising: a pump body; a pump door; and an infusion switching mechanism, an exhaust device and a bubble detection device which are arranged on the pump body;

an installation panel is formed at the front end of the pump body, and the pump door is movably connected with the installation panel to open or close the installation panel; the installation panel is connected with an infusion consumable to form a placement slot for placing the infusion consumable, the infusion consumable includes a multi-way connection joint and a plurality of upper branch tubes and one main tube respectively connected to both ends of the multi-way connection joint, the multi-way connection joint includes N branch tube joints and 1 main tube joint, wherein N≥2;

the infusion switching mechanism includes a multi-channel liquid-stopping clamp, a liquid-stopping clamp fixing base and a driving structure, wherein the liquid-stopping clamp fixing base is fixed on the installation panel, the front end of the liquid-stopping clamp fixing base is provided with an insertion slot into which the multi-channel liquid-stopping clamp is inserted, the pump door is provided with a sliding slot for the multi-channel liquid-stopping clamp to slide, and the insertion slot and the sliding slot cooperate to form a sliding channel;

the multi-channel liquid-stopping clamp includes a body and N channels formed on the body, each channel includes a liquid-passing section and a liquid-stopping section, wherein the liquid-passing section and the liquid-stopping section on each channel are arranged in a manner that any one of the upper branch tubes is located on the liquid-passing section of the corresponding channel while other upper branch tubes are located on the liquid-stopping section of the corresponding channel during the infusion;

the driving structure is arranged at the upper end of the pump body and movably connected with the multi-channel liquid-stopping clamp for driving the multi-channel liquid-stopping clamp to move back and forth along the sliding channel, so as to make the upper branch tubes selectively communicate with the main tube;

the exhaust device is used for squeezing the main tube to exhaust air in the main tube; and the bubble detection device is arranged on the installation panel and includes N upper branch tube bubble detection devices and one main tube bubble detection device.

2. The multi-channel automatic infusion pump according to claim 1, wherein the infusion switching mechanism further comprises a detection plate arranged above the driving structure, the detection plate is provided with a sliding rheostat, and the driving structure is provided with a position detection point, and a sliding contact of the sliding rheostat is ganged-linked with the position detection point.

3. The multi-channel automatic infusion pump according to claim 2, wherein the driving structure comprises: a motor; a push rod, a push rod attachment arm and a spring arranged in the liquid-stopping clamp fixing base, wherein the motor is connected with the rear end of the liquid-stopping clamp fixing base, the push rod is connected with the motor, the push rod attachment arm is movably arranged on both sides of the push rod, the spring is arranged between the rear end of the push rod attachment arm and the push rod, and a bent part is formed at the front end of the push rod attachment arm;

the multi-channel liquid-stopping clamp is formed with a recessed part that matches the bent part;

the insertion slot is arranged such that under the drive of the motor, the push rod attachment arm can be selectively combined with and separated from the multi-channel liquid-stopping clamp; and the position detection point is arranged on the push rod.

4. The multi-channel automatic infusion pump according to claim 1, wherein the main tube is provided with a two-way connection joint.

5. The multi-channel automatic infusion pump according to claim 1, wherein the sliding slot is provided with an elastic support structure in contact with the multi-channel liquid-stopping clamp, the elastic support structure includes two connecting rods and a supporting plate movably connected with two connecting rods, and a spring is arranged between the supporting plate and the connecting rod.

6. The multi-channel automatic infusion pump according to claim 1, further comprising a mechanical liquid-stopping clamp, wherein the mechanical liquid-stopping clamp is arranged at the lower end of the pump body for cooperating with the pump door so that the main tube is in a liquid-passing state or liquid-stopping state.

7. The multi-channel automatic infusion pump according to claim 1, wherein the mechanical liquid-stopping clamp comprises a mechanical liquid-stopping clamp fixing base; a liquid-stopping knife clamp, a knife clamp spring, a liquid-stopping push rod and a push rod spring arranged on the mechanical liquid-stopping clamp fixing base; the front end of the liquid-stopping push rod extends out of the installation panel through the front end of the mechanical liquid-stopping clamp fixing base, and the rear end is connected with that of the mechanical liquid-stopping clamp fixing base through the push rod spring; the liquid-stopping knife clamp includes a liquid-stopping portion and a connecting portion connected by a connecting shaft, wherein the connecting portion is movably connected with the rear end of the liquid-stopping push rod, and the front end of the liquid-stopping portion is formed with a bent part, the pump door is formed with a limiting slot adapted to the bent part; the knife clamp spring is arranged between the rear end of the liquid-stopping part and the mechanical stop clamp fixing base.

8. The multi-channel automatic infusion pump according to claim 5, wherein the rear end of the liquid-stopping push rod is formed with a hook that hooks the connecting portion.

9. The multi-channel automatic infusion pump according to claim 1, further comprising a controller, which is respectively communicatively connected with the exhaust device, the bubble detection device and the driving structure;

for the two adjacent upper branch tubes A and B, when the infusion of the upper branch tube A is the basic drug and the infusion of the upper branch tube B is the added therapeutic drug, the controller executes a control instruction to achieve the following steps:

S100: sending a first infusion instruction to the driving structure to drive the upper branch tube A to start the infusion while prohibiting infusion in the upper branch tube B;

S200: acquiring the infusion mass M of the upper branch tube A in real time; if M>D, executing step S300; if M<=D, continuing to execute step S200; wherein D is the first infusion mass of the basic drug set in medicine; and S300: sending a second infusion instruction to the driving structure to drive the upper branch tube B to start the infusion while prohibiting infusion in the upper branch tube A.

10. The multi-channel automatic infusion pump according to claim 9, further comprising the following steps:

S400: receiving detection data sent by the upper branch tube bubble detection device to which the upper branch tube B belongs in real time, and executing step S500 when the upper branch tube B is determined to have completed the infusion based on the received detection data; otherwise, continuing to execute step S400;

S500: sending a first infusion instruction to the driving structure to drive the upper branch tube A to start the infusion while prohibiting infusion in the upper branch tube B; and S600: receiving detection data sent by the upper branch tube bubble detection device to which the upper branch tube A belongs in real time, and controlling the upper branch tube A to stop the infusion when the upper branch tube A is determined to have completed the infusion based on the received detection data; otherwise, continuing to execute step S600.

\* \* \* \* \*